United States Patent
Lee et al.

(10) Patent No.: US 9,123,120 B2
(45) Date of Patent: Sep. 1, 2015

(54) PROGRESSIVE DECISION FOR CELLULAR PROCESS SELECTION

(75) Inventors: Shih-Jong J. Lee, Bellevue, WA (US); Samuel V. Alworth, Seattle, WA (US)

(73) Assignee: DR Vision Technologies LLC, Bellevue, WA (US)

( * ) Notice: Subject to any disclaimer, the term of this patent is extended or adjusted under 35 U.S.C. 154(b) by 512 days.

(21) Appl. No.: 13/573,136

(22) Filed: Aug. 24, 2012

(65) Prior Publication Data

US 2014/0056504 A1    Feb. 27, 2014

(51) Int. Cl.
| | |
|---|---|
| G06T 7/00 | (2006.01) |
| G01N 33/50 | (2006.01) |
| G06K 9/00 | (2006.01) |
| C12M 1/34 | (2006.01) |
| C12M 1/36 | (2006.01) |

(52) U.S. Cl.
CPC .............. *G06T 7/0081* (2013.01); *C12M 41/36* (2013.01); *C12M 41/48* (2013.01); *G01N 33/5005* (2013.01); *G06K 9/00127* (2013.01); *G06T 7/0012* (2013.01); *G06T 7/0097* (2013.01); *G06T 2207/30024* (2013.01)

(58) Field of Classification Search
CPC .......... G06T 2207/30024; G06T 2207/10056; G06T 7/0012; G06T 7/0081; G06T 2207/30004; G06T 2207/20141; G06K 9/00127; G06K 9/00147; G06K 9/00288; G06K 9/342; G06K 9/6218; G01N 33/5005; G01N 33/505; G01N 2015/008; G01N 2018/1006; C12M 41/46; C12M 41/48; C12M 41/36; A61B 5/14546
See application file for complete search history.

(56) References Cited

U.S. PATENT DOCUMENTS

| | | | |
|---|---|---|---|
| 5,757,954 A * | 5/1998 | Kuan et al. | 382/133 |
| 5,991,028 A * | 11/1999 | Cabib et al. | 356/456 |
| 6,327,377 B1 * | 12/2001 | Rutenberg et al. | 382/133 |
| 6,463,175 B1 | 10/2002 | Lee | |
| 6,681,046 B1 * | 1/2004 | Kashiwagi et al. | 382/195 |
| 7,203,360 B2 | 4/2007 | Lee et al. | |
| 7,369,696 B2 * | 5/2008 | Arini et al. | 382/133 |
| 7,483,554 B2 * | 1/2009 | Kotsianti et al. | 382/128 |
| 7,689,038 B2 * | 3/2010 | Zahniser | 382/180 |
| 7,711,174 B2 * | 5/2010 | Sammak et al. | 382/133 |
| 7,776,584 B2 * | 8/2010 | Richmond et al. | 435/309.1 |
| 7,796,815 B2 * | 9/2010 | Muschler et al. | 382/173 |
| 7,907,769 B2 * | 3/2011 | Sammak et al. | 382/133 |
| 7,920,736 B2 * | 4/2011 | Sammak et al. | 382/133 |
| 7,974,464 B2 | 7/2011 | Lee et al. | |
| 8,014,590 B2 | 9/2011 | Lee et al. | |
| 8,189,900 B2 * | 5/2012 | Sammak et al. | 382/133 |
| 8,265,357 B2 * | 9/2012 | Ramsing et al. | 382/128 |
| 8,340,389 B2 * | 12/2012 | Kincaid | 382/133 |

OTHER PUBLICATIONS

Alworth, et al, "Real-time scoring of human iPSC differentiation potential using live-cell microscopy and image recog", Poster presentation, 10th ISSCR Annual Meeting, Jun. 20.

* cited by examiner

*Primary Examiner* — Manav Seth

(57) ABSTRACT

A computerized image guided biological cellular process progressive selection method receives at least one state cell image. A state cell region recognition is performed using the state cell image to generate state cell region output. A state cell measurement is performed using the state cell region to generate at least one state cell feature output. A state cell decision is performed using the state cell feature to generate state cell selection decision output. The selected cell is progressively selected in at least one follow-on states by its image guided state cell selection method. The method further includes at least one additional image acquired in a later frame of same state and state cell feature includes temporal features of growth patterns.

21 Claims, 11 Drawing Sheets

PROGRESSIVE DECISION FOR CELLULAR PROCESS SELECTION

GOVERNMENT INTERESTS

Statement as to Rights to Inventions Made Under Federally Sponsored Research and Development This work was supported by U.S. Government grant numbers 4R44HL106863-02, awarded by the National Heart, Lung, and Blood Institutes. The U.S. Government may have certain rights in the invention.

TECHNICAL FIELD

This invention relates to the cell selection for biological cellular processes such as stem cell production and differentiation, cell culture production and cell transformation assays.

BACKGROUND OF THE INVENTION

The advancement in biological cellular process technologies allows the reprogramming of matured cells such as somatic cells to an embryonic-like state. These "induced pluripotent stem cells" (iPSCs) enable a new patient-specific or "personalized" medicine paradigm in 1) autologous regenerative medicine, 2) disease cell lines from patient cells for more predictive assays in drug discovery and basic research, and 3) patient-specific cell generation for personalized diagnostic and drug efficacy or adverse effects testing. To achieve the promise of iPSC technology requires the controlled differentiation of iPSCs to specific lineages.

However, the yields of reprogramming and differentiation are both very low. For any given matured cells under reprogramming, it is not at all certain that any significant number of iPSCs will be produced. Similarly, for any given iPSC colony under differentiation, it is not at all certain that any significant number of target cells will be produced.

To mitigate the low yield and the lack of certainty, state-of-art protocols require a large number of samples to carry out the full reprogramming process, and selection of more iPSC colonies for expansion and characterization than is desirable. For the differentiation process, iPSC lines are selected in an ad-hoc fashion and a large number of stem cells are used for differentiation in the hope of generating a sufficient quantity of target cells. This approach is time consuming and expensive as reflected by the prices of iPSC derived cells costing more than 10× the price of adult human primary fibroblasts.

For the reprogramming process, iPSC colony selection is largely done manually with additional staining such as TRA-1-60 surface marker or using viral-GFP silencing when available. However, additional staining is not desirable in practical clinical laboratory settings. Therefore, it is desirable to make the selection using non-invasive imaging modalities such as phase contrast images. There are computer image recognition methods that are developed to determine between iPSCs and Non-iPSCs. The prior art methods are based on fixed images acquired near the end of reprogramming. Therefore, many colonies have to go through the full course of reprogramming which is costly and inefficient. To date, there are no effective image recognition methods that can predict the outcomes of the differentiation process.

Reprogramming for induced pluripotent stem cells (iP-SCs) is a slow process. It takes around 4 weeks for reprogrammed cells to reach a pluripotent state. In the process many colonies are formed, but only a small number of them are true iPSC colonies. The current practice selects true iPSC colonies near the end of the reprogramming process (harvesting time). The selection could be done using morphological criteria from the microscopy images of the colonies either by human eye or by computer image analysis. Another selection method uses the images of additional staining such as TRA-1-60 surface marker or viral GFP-silencing to assist the determination of iPSC colonies from non-iPSC ones. In addition, the iPSC PCR Array is used to analyze multiple biologically validated pluripotency biomarkers to distinguish fully reprogrammed iPSC colonies from partially reprogrammed ones. There are many issues with the current practices as listed below:

1. Morphological criteria are non-specific at harvesting time. There are many non iPSC colonies with similar appearance to iPSC colonies that could confuse the selection;
2. At harvesting time, the grown colonies could merge or interfere with each other. Therefore, true iPSC colonies could be mixed with or contaminated by non-iPSC colonies;
3. Colonies are not necessarily synchronized in the reprogramming process. At a fixed harvesting time, some colonies may not have fully reprogrammed and some may have passed the iPSC state and have spontaneously differentiated;
4. It is unnecessarily costly to select multiple iPSC colonies. More accurate, specific selection could reduce the number of colonies required;
5. It is wasteful to process the large number of non-productive colonies through the whole reprogramming process.

We discovered an early kinetic pattern of colony formation for cells undergoing reprogramming, within the first 72 hours after a colony is first discernible. The kinetic pattern can reliably predict which cells will most likely progress to become induced pluripotent stem (iPS) cell colonies (See Hendrik et al "Assessment of an imaging protocol for real-time selection of human iPSC colonies using live cell microscopy and image recognition software", poster presentation at the ISSCR $10^{th}$ Annual Meeting, June 2012). Similar early kinetic patterns can also accurately predict which colonies will most likely differentiate with good cardiomyocyte yield (Alworth et al., "Real-time scoring of human iPSC differentiation potential using live-cell microscopy and image recognition software", poster presentation at the ISSCR $10^{th}$ Annual Meeting, June 2012). Studies in the field have focused on late colony morphology at around three weeks, or the use of surface markers for iPS selection. The quantification of colony formation dynamics could generate powerful kinetic image features that can be used reliably for real-time colony outcome prediction in a much earlier stage of reprogramming. The outcomes include not only iPSCs formation but also prediction of differentiation yield.

Objects and Advantages

This invention provides a method that selects colonies starting from early states, rather than waiting until the colonies are fully reprogrammed. This uniquely allows the progressive selection of colonies. That is, a colony selected during the pre-colony state decision can be subjected to the selection decision in the colony emerging state, and the selection process could continue progressively to the next state. The progressive selection method of the current invention can address all the above issues in the current practice.

1. The decision at different states takes advantage of the unique morphological and kinetic colony formation patterns at different states through out the reprogramming process rather than relying solely on their appearance at harvesting time. This achieves high confidence selection outcome;

2. Only a small number of selected colonies are considered and non-selected colonies can be removed if they are at close proximity of the selected colonies. This avoids the mixing and contamination by other colonies;
3. The progressive selection method allows an individual colony to be progressively selected independent of the timing of other colonies. This avoids the asynchronous problem;
4. Only a small number of previously selected colonies need to be processed through new selection process. This could dramatically reduce the selection time and cost;
5. Non-selected colonies could be rejected and discontinued very early to avoid wasteful processing.

The progressive selection method of the current invention is applicable not only to iPSC reprogramming processes but also to biological cellular processes such as stem cell (both iPSC and embryonic stem cell) production, stem cell differentiation, cell culture production and cell transformation assays, etc.

The primary objective of the invention is to provide a highly accurate and efficient colony selection method for iPSC reprogramming. The second objective of this invention is to provide a highly accurate and efficient cell selection method for stem cell differentiation. The third objective of this invention is to provide a highly accurate and efficient cell selection method for biological cellular processes. The fourth objective of this invention is to provide a progressive selection method to reduce the selection cost. The fifth objective of this invention is to provide a progressive selection method to avoid wasteful processing.

SUMMARY OF THE INVENTION

A computerized image guided biological cellular process progressive selection method receives at least one state cell image. A state cell region recognition is performed using the state cell image to generate state cell region output. A state cell measurement is performed using the state cell region to generate at least one state cell feature output. A state cell decision is performed using the state cell feature to generate state cell selection decision output. The selected cell is progressively selected in at least one follow-on states by its image guided state cell selection method. The method further includes at least one additional image acquired in a later frame of same state and state cell feature includes temporal features of growth patterns.

BRIEF DESCRIPTION OF THE DRAWINGS

The preferred embodiment and other aspects of the invention will become apparent from the following detailed description of the invention when read in conjunction with the accompanying drawings, which are provided for the purpose of describing embodiments of the invention and not for limiting same, in which.

DETAILED DESCRIPTION OF THE INVENTION

I. Application Scenarios

Figure 1:
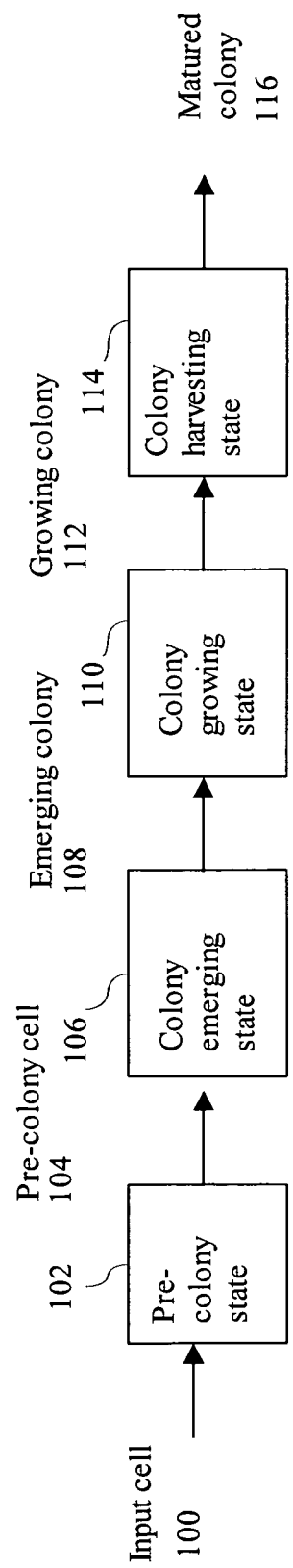
FIG. 1 shows the morphological states in a reprogramming process.

A reprogramming process consists of morphological states that can be identified visually or by computer image recognition as shown in FIG. 1. In the course of the reprogramming, some input cells 100 reach the pre-colony state 102. Continuing-on, some pre-colony cells 104 progress into the colony emerging state 106 where emerging colonies 108 are formed. Some of the emerging colonies 108 will grow over time in the colony growing state 110 to form growing colonies 112 until the colonies reach the colony harvesting state 114 having matured colonies 116.

Our invention selects colonies starting from early states rather than wait until the reprogramming process nears its end. This uniquely allows the progressive selection of colonies. That is, a colony selected during the pre-colony state decision can be subjected to the selection decision in the colony emerging state and the selection process can continue progressively to the next state.

Figure 2:
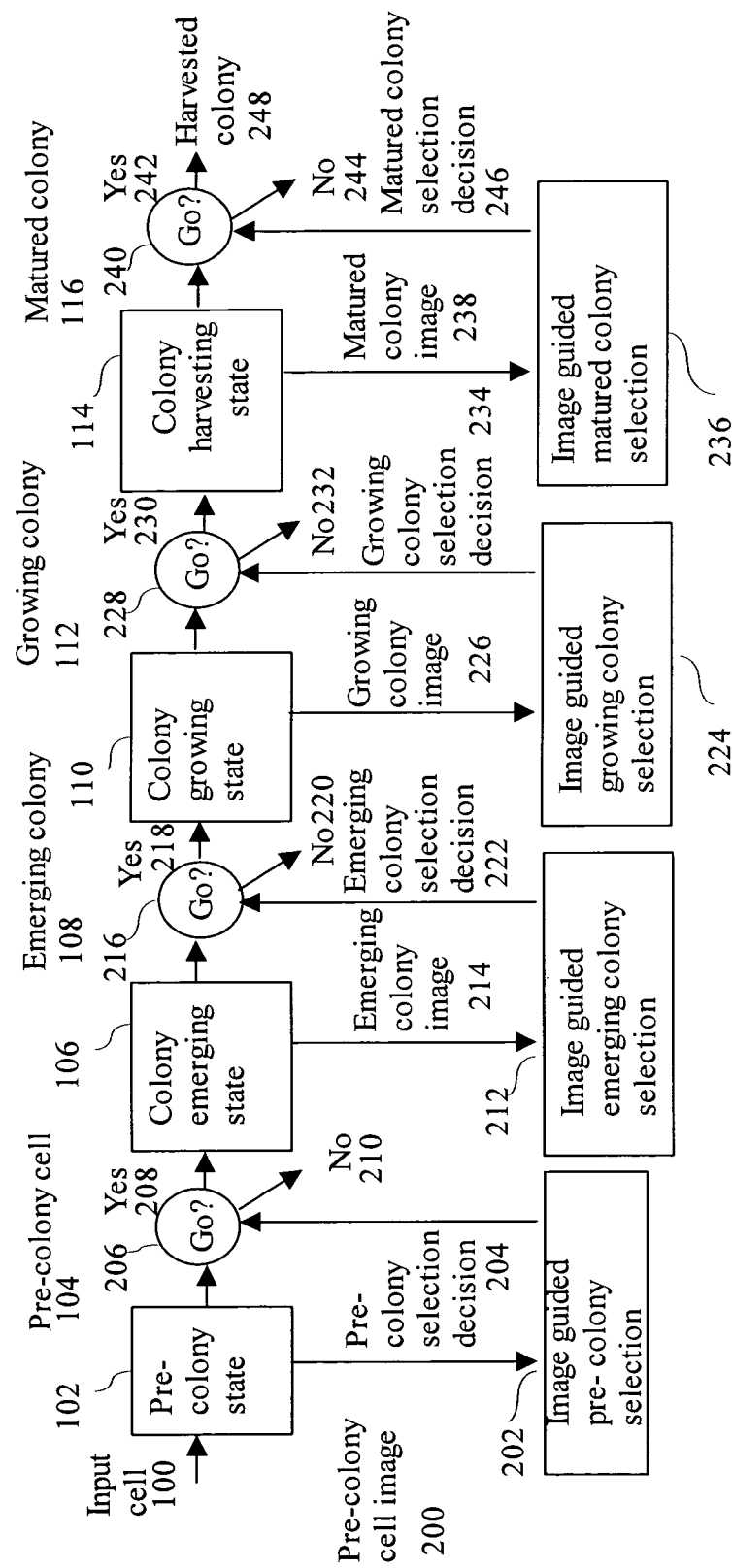
FIG. 2 shows the processing flow for the progressive selection method in one embodiment of the application scenario.

FIG. 2 illustrates the progressive selection method. During the pre-colony state 102, pre-colony cell image 204 is subjected to image guided pre-colony selection 202. The pre-colony cells 104 with a pre-colony selection decision 204 outcome corresponding to "Yes" 208 in the "Go" 206 decision will continue the reprogramming and selection process. The pre-colony cells 104 with a pre-colony selection decision 204 outcome corresponding to "NO" 210 in the "Go" 206 decision will not be selected and the reprogramming process could continue or could be abandoned if it is practically convenient to do so. After the selected pre-colony cells have progressed to the colony emerging state 106, the emerging colony image 214 are subjected to image guided emerging colony selection 212. The emerging colonies 108 with an emerging colony selection decision 222 outcome corresponding to "Yes" 218 in the "Go" decision 216 will continue the reprogramming and selection process. The emerging colonies 108 with an emerging colony selection decision 222 outcome corresponding to "NO" 220 in the "Go" decision 216 will not be selected and the reprogramming process could continue or could be abandoned if it is practically convenient to do so.

After the selected emerging colonies 108 have progressed to the colony growing state 110, the growing colony image 226 is subjected to image guided growing colony selection 224. The growing colonies 112 with an image guided growing colony decision 224 outcome corresponding to "Yes" 230 in the "Go" decision 228 will continue the reprogramming and selection process. The growing colonies 112 with an image guided growing colony decision 224 outcome corresponding to "NO" 232 on the "Go" decision 228 will not be selected and the reprogramming process could continue or could be abandoned if it is practically convenient to do so. Similarly, after the selected growing colonies 112 have progressed to the colony harvesting state 114, the matured colony image 238 are subjected to image guided matured colony selection 236. The matured colonies 116 with a matured colony selection decision 244 outcome corresponding to "Yes" 242 in the "Go" decision 240 will be harvested as the harvested colony 248. That could be picked and expanded to create iPSC lines. The matured colonies 116 with a matured colony selection decision 244 outcome corresponding to "NO" 244 in the "Go" decision 240 will not be harvested.

II. Pre-Colony State Decision

II.1 Overview

Figure 3:
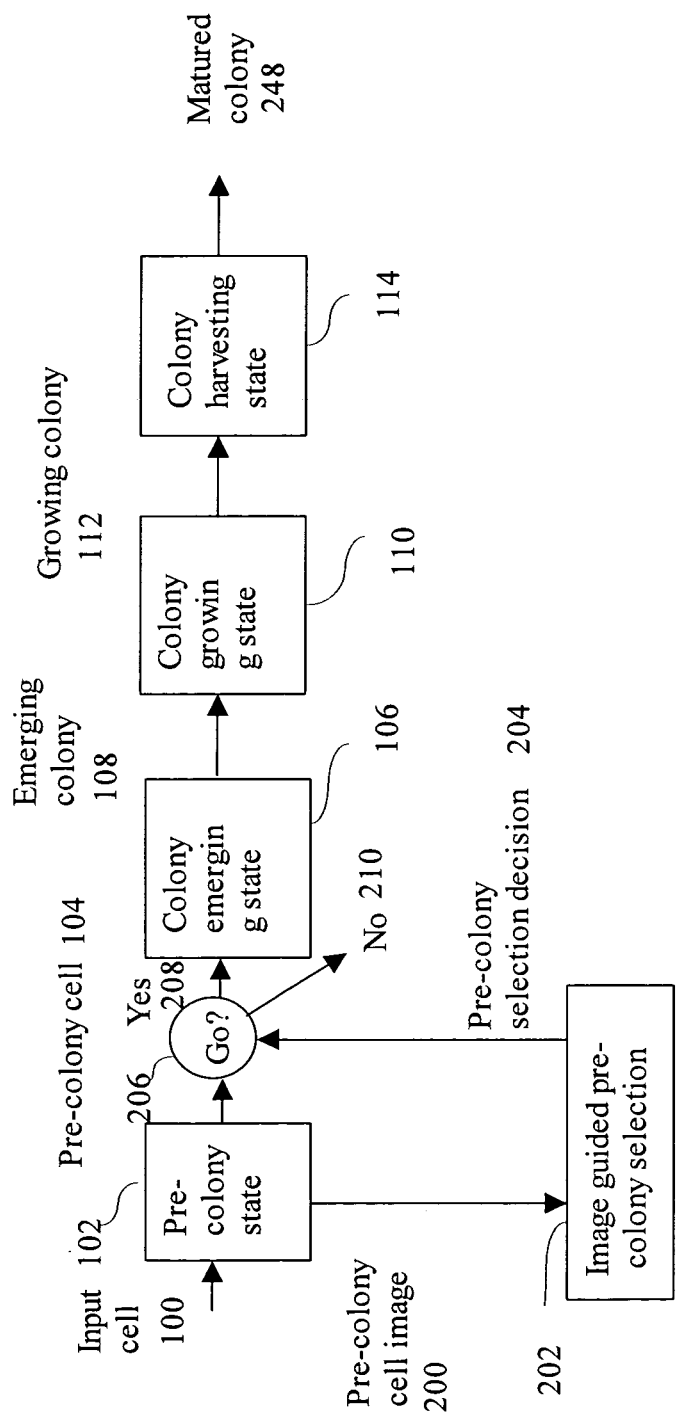
FIG. 3 shows the processing flow for the pre-colony state decision method of the current invention.

The early cellular patterns in the pre-colony state 102 can be used to perform pre-colony selection decision 204 through an image guided pre-colony selection method 202. FIG. 3 shows the processing flow for the pre-colony state decision 204 of the current invention. The input cell 100 is reprogrammed to the pre-colony state 102. A pre-colony cell image 200 is acquired and processed by the image guided pre-colony selection 202 step to generate a pre-colony selection decision 204. The pre-colony selection decision 204 is used to make a "Go" decision 206. If the decision is "Yes" 208, the pre-colony cell 104 is continued with the reprogramming process to reach the colony emerging state 106. If the decision is "No" 210, no further selection decision will be made to the pre-colony cell 104 and depending on the assay protocol, the reprogramming may stop on the rejected pre-colony cells to reduce wasteful processing cost.

II.2 Image Guided Pre-Colony Selection

Figure 4:
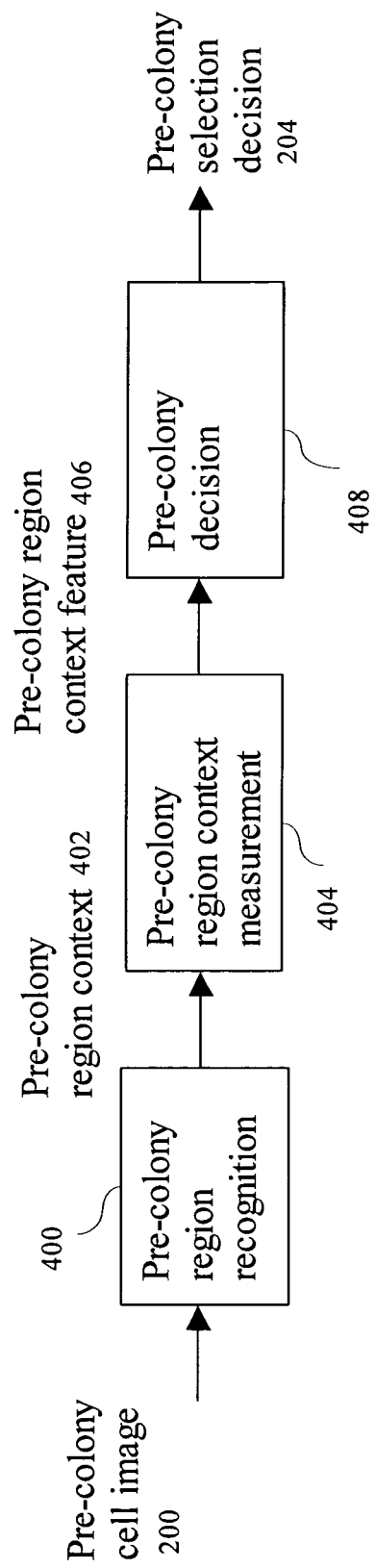
FIG. 4 shows the processing flow for the image guided pre-colony selection method.

As shown in FIG. 4, a computerized image guided pre-colony selection method inputs at least one pre-colony cell image 200. It performs pre-colony region recognition 400 using the pre-colony cell image 200 to generate pre-colony region context 402 output. It then performs pre-colony region context measurement 404 using the pre-colony region context 402 to generate at least one pre-colony region context feature 406 output. At least one pre-colony region context feature 406 is used to perform pre-colony decision 408 that generates pre-colony selection decision 204 output.

A. Pre-Colony Region Recognition

Figure 5:
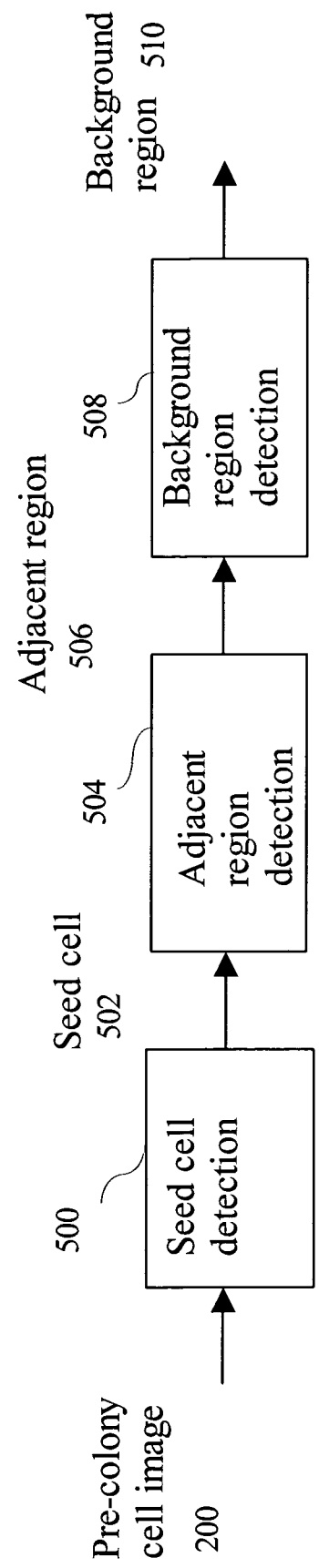
FIG. 5 shows the processing flow for the pre-colony region recognition method.

As shown in FIG. 5, pre-colony region recognition method performs seed cell detection 500 to detect at least one seed cell 502 that would advance to form a colony. In one embodiment of the invention, the seed cell 502 is detected using the learnable object segmentation method (Lee et al "learnable object segmentation", U.S. Pat. No. 7,203,360) and refined by the structure-guided image processing and image feature enhancement method (Lee, "Structure-guided image processing and image feature enhancement", U.S. Pat. No. 6,463,175) guided by the method of directed pattern enhancement (Lee et al, "Method of directed pattern enhancement for flexible recognition" U.S. Pat. Nos. 7,974,464 and 8,014,590). After the seed cell 502 is detected, the region adjacent to the seed cell is detected by an adjacent region detection 504 step. In one embodiment of invention, adjacent region 506 could be detected by simple dilation of the seed cell 504 by a desired adjacent region size parameter. In another embodiment of the invention, surrounding cells of the seed cell 502 are detected and the regions occupied by the surrounding cells are detected as the adjacent region 506. In yet another embodiment of the invention, the surrounding cells occupied regions are dilated to form the adjacent region 506. The pre-colony region context 402 contains the seed cell 502 and the adjacent region 506. In another embodiment of the invention, a background region detection 508 is performed to detect cellular background region and include the background region 510 in the pre-colony region context 402.

To improve the seed cell detection 500 accuracy, in another embodiment of the invention, the pre-colony cell image 200 includes at least one additional future-frame image that is acquired after colony is emerged. Therefore, the seed cell detection 500 can be guided by the already formed emerging colony in a backward detection fashion. An image alignment may be performed between the pre-colony cell image 200 and emerging colony image 214. After alignment, the seed cell detection 500 is performed within a region in pre-colony cell image 200 that is in close proximity to the location of the corresponding colony in the emerging colony image 214.

B. Pre-Colony Region Context Measurement

Pre-colony region context 402 is used to measure at least one pre-colony region context feature 406 from a set of pre-cursory features. The feature set includes seed cell features, adjacent region context features and background context features.

i. Seed Cell Features

In one embodiment of the invention, seed cell features include seed cell type, its morphological measures such as shape (compactness, elongateness, major-minor length ratio, Fourier descriptors, etc.) and size (area, perimeter, major and minor axis lengths, etc.); intensity measures (mean, median, standard deviation, max, min, percentiles, etc.) and texture measures (co-occurrence matrix derived features, run-length derived features, wavelet derived features, fractal derived features, etc.). If the seed cell region contains multi nuclei, the multi-nuclear structures can be measured. The multi-nuclear structure measures include the density, symmetry (mean and standard deviation of the distances between nuclear centers), amount of overlap among multi nuclei, etc.

If there are more than one imaging modalities, such as phase contrast, DIC, fluorescence, luminescence or color channels. Multi-spectrum or color features can also be included for intensity and texture measures.

ii. Adjacent Region Context Features

In one embodiment of the invention, the adjacent region context features include intensity, texture and multi-spectrum measures for the adjacent region as a whole. If there are surrounding cells in the adjacent region, the population statistics (mean, median, standard deviation, etc.) of the size, shape, intensity and texture measures for the surrounding cells as a group can be measured. The ratio or difference between the measures of the seed cell and the adjacent region population statistics can be calculated as context features.

Also, inter-cellar crowdness measures such as the mean and standard deviation of the distances between cell centers can be included.

iii. Background Context Features

In the embodiment of the invention where background region 510 is detected. The background context features include intensity, texture and multi-spectrum measures for the background region 510 as a whole. The ratio or difference between the measures of the adjacent region 506 and background region 510 can be calculated as context features.

In the embodiment where the pre-colony cell image includes future-frame image that is acquired after colony is emerged, the changes in seed cell features, adjacent region context features and background context features can be measured as the temporal features. If time-lapse image is available, the temporal measures include the starting time of pre-colony state 102 since the starting of the reprogramming and seed cell lineage measures such as cell division rate, average time of cell division, linage symmetry, etc. The temporal measures could include temporal velocity (if at least 3 frames are available) and acceleration (if at least 4 frames are available) of the changes.

In addition, if 3D image is available the measures can be directly extended to 3D. For example all length measures are in 3D and area becomes volume.

C. Pre-Colony Decision

The pre-colony decision 408 step uses at least one pre-colony region context feature 406 to make a pre-colony selection decision 204. In one embodiment of the invention, the selection decision is reprogramming outcomes such as "iPSC" vs. "Non-iPSC". "iPSC" decision is for predicting pre-colony cell that is likely to be successfully re-programmed into induced pluripotent stem cells. "Non-iPSC" decision is for predicting pre-colony cell that is unlikely to be successfully re-programmed into induced pluripotent stem cells. In another embodiment of the invention, the selection decision is differentiation outcomes such as "Differentiable" vs. "Non-Differentiable". "Differentiable" decision is for predicting pre-colony cell that is likely to be successfully differentiated into the desired cell type(s). "Non-Differentiable" decision is for predicting pre-colony cell that is unlikely to be successfully differentiated into the desired cell type(s). The differentiation can be performed either by direct programming that bypass the follow-on reprogramming process or by first reprogrammed into iPSC or partial iPSC and then expanded and differentiated into the desired cell types. The desired cell types include, without limitation, neurons, cardiomyocytes, blood cells, hepatocytes, pancreatic cells, muscle cells, lung cells, etc.

In one embodiment of the invention, the pre-colony decision is performed by the hierarchic decision method such as regulation tree (Lee, "Regulation of hierarchic decisions in intelligent systems", U.S. Pat. No. 7,031,948, Apr. 18, 2006 and Lee, "Information integration method for decision regulation in hierarchic decision systems", U.S. Pat. No. 7,293,000, Nov. 6, 2007). Those ordinary skilled in the art should recognize that other pattern classification methods such as linear classifiers, support vector machines, quadratic classifiers, kernel estimation methods, boosting, artificial neural networks, gene expression programming, Bayesian networks, etc. are all within the scope of the current invention.

In another embodiment of the invention, the decision method does not output a crisp decision, that is binary ('Yes", "No") decision. Instead a score is output from the decision method. The score can then be thresholded for a binary decision. In this case, the threshold level can be used to control the sensitivity and specificity (or positive predictive value) of the decision output. In this embodiment, a threshold can be set to have very high positive predictive value even if the sensitivity is low. This allows the selection of just a few very high confident pre-colony cells for continued processing.

D. Progressive Decision

The pre-colony cell 104 that is selected for continued processing by the pre-colony selection decision 204 will likely progress to the colony emerging state 106. It can be further selected progressively by the emerging colony state decision method described in the next section.

III. Emerging Colony State Decision

III.1 Overview

Figure 6:
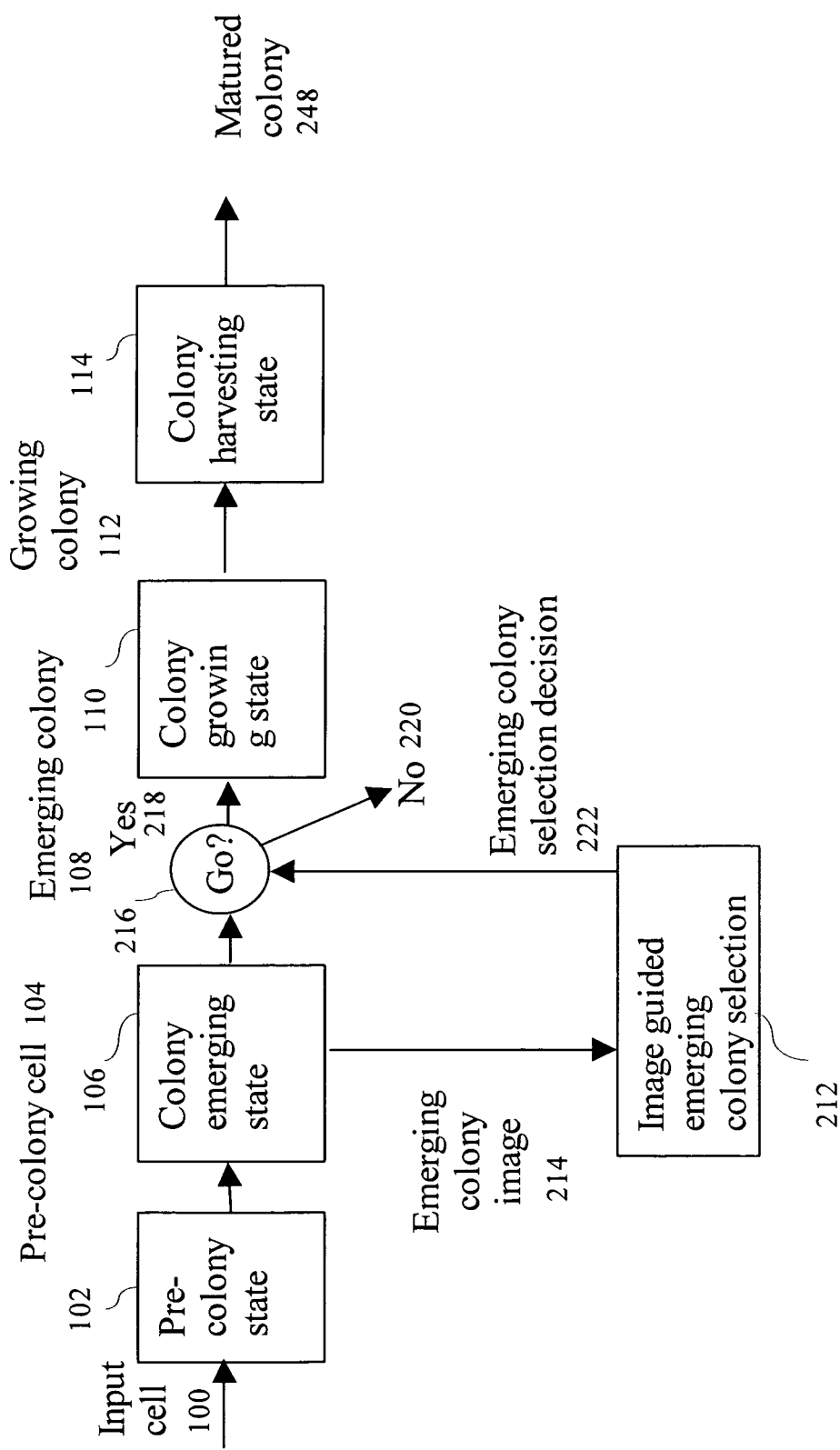
FIG. 6 shows the processing flow for the emerging colony state decision method of the current invention.

The colony emerging patterns in the colony emerging state can be used to perform emerging colony selection decision through an image guided emerging colony selection method. FIG. 6 shows the processing flow for the emerging colony state decision of the current invention. The input cell 100 is reprogrammed to the colony emerging state 106. An emerging colony cell image 214 is acquired and processed by the image guided emerging colony selection 212 step to generate an emerging colony selection decision 222. The emerging colony selection decision 222 is used to make a "Go" decision 216. If the decision is "Yes" 218, the emerging colony 108 is continued reprogrammed to reach the colony growing state 110. If the decision is "No" 220, no further selection decision will be made to the emerging colony 108 and depending on the assay protocol, the reprogramming may stop on the rejected emerging colony to reduce wasteful processing cost.

III.2 Image Guided Emerging Colony Selection

Figure 7:
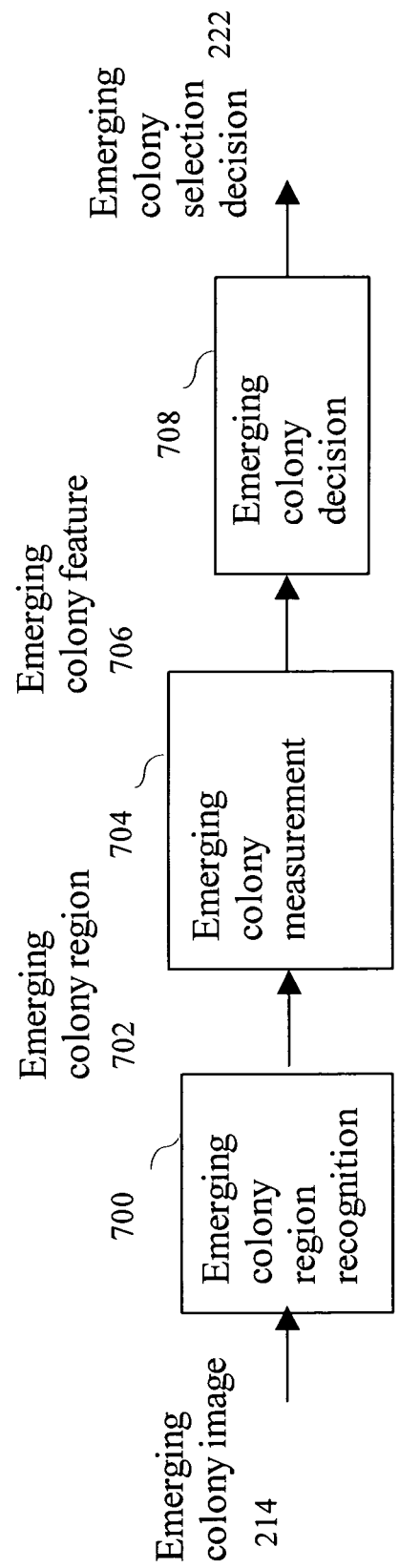
FIG. 7 shows the processing flow for the image guided emerging colony selection method.

As shown in FIG. 7, a computerized image guided emerging colony selection method inputs at least one emerging colony cell image. It performs emerging colony region recognition using the emerging colony image 214 to generate emerging colony region 702 output. It then performs emerging colony measurement 704 using the emerging colony region 702 to generate at least one emerging colony feature 706 output. At least one emerging colony feature 706 is used to perform emerging colony decision 708 that generates emerging colony selection decision 222 output.

A. Emerging Colony Region Recognition

Emerging colony region recognition method performs emerging colony detection to detect the region of the emerging colony. In one embodiment of the invention, the emerging colony is detected using the learnable object segmentation method (Lee et al "learnable object segmentation", U.S. Pat. No. 7,203,360) and refined by the structure-guided image processing and image feature enhancement method (Lee, "Structure-guided image processing and image feature enhancement", U.S. Pat. No. 6,463,175) guided by the method of directed pattern enhancement (Lee et al, "Method of directed pattern enhancement for flexible recognition" U.S. Pat. Nos. 7,974,464 and 8,014,590).

To improve the emerging colony detection accuracy, in another embodiment of the invention, the emerging colony image 214 further includes at least one additional image acquired in a later frame in colony emerging state 106. Therefore, the emerging colony detection of the early frame image can be guided by the better formed emerging colony in the later frame. An image alignment may be performed between the early and later frame images. After the alignment, the emerging colony detection is performed within a region in early frame image that is in close proximity to the location of the corresponding colony in the later frame image. This also serves as a cross check for the emerging colony detection in the later frame.

B. Emerging Colony Measurement

Emerging colony region is used to measure at least one emerging colony feature from a set of emerging colony features. In one embodiment of the invention, the feature set includes morphological measures such as shape (compactness, elongateness, major-minor length ratio, Fourier descriptors, etc.) and size (area, perimeter, major and minor axis lengths, etc.); intensity measures (mean, median, standard variation, max, min, percentiles, etc.) and texture measures (co-occurrence matrix derived features, run-length derived features, wavelet derived features, fractal derived features, etc.). If the emerging colony region contains multiple components, the number of components and the multi-component structures are measured. The multi-component structure measures include the population statistics (mean, median, standard deviation, etc.) of the size, shape, intensity and texture measures for the components as a group.

If there are more than one imaging modalities, such as phase contrast, DIC, fluorescence, luminescence and color channels. Color or multi-spectrum features can also be included for intensity and texture measures.

In the embodiment where the emerging colony cell image further includes at least one additional image acquired in a later frame in colony emerging state, the temporal changes in emerging colony features can be measured as the growth pattern temporal features. The measure of radius growth along the angular axis of the polar coordinate (mean and standard deviation) can reflect the rate of area change and the symmetry of the area changes. The symmetry of the area changes is an especially important feature as some colonies form as the steady emergence of a small dense core. Other types of colonies emerge all at once, and from multiple regions.

If time-lapse image is available, the temporal measures include the starting time of the emerging colony state since the starting of the reprogramming and emerging colony kinetic measures such as growth rate, growth structure, etc. The temporal measures could include temporal velocity (if at least 3 frames are available) and acceleration (if at least 4 frames are available) of the feature changes.

In addition, if 3D image is available the measures can be directly extended to 3D. For example all length measures are in 3D and area becomes volume.

If the emerging colony 108 has previously passed the image guided pre-colony selection 202, the emerging colony features 706 can be enriched with the pre-colony region context features 406 measured during the pre-colony state 102. The enriched feature set including both emerging colony features 706 and pre-colony region context features 406 can be used for the emerging colony selection decision 222.

C. Emerging Colony Decision

The emerging colony decision 708 step uses at least one emerging colony feature 706 to make an emerging colony selection decision 222. In one embodiment of the invention, the selection decision is reprogramming outcomes such as "iPSC" vs. "Non-iPSC". "iPSC" decision is for predicting emerging colony 108 that is likely to be successfully re-programmed into induced pluripotent stem cells. "Non-iPSC" decision is for predicting emerging colony 108 that is unlikely to be successfully re-programmed into induced pluripotent stem cells. In another embodiment of the invention, the selection decision is differentiation outcomes such as "Differentiable" vs. "Non-Differentiable". "Differentiable" decision is for predicting emerging colony 108 that is likely to be successfully differentiated into the desired cell type(s). "Non-Differentiable" decision is for predicting emerging colony that is unlikely to be successfully differentiated into the desired cell type(s). The differentiation can be performed either by direct programming that bypass the follow-on reprogramming process or by first reprogrammed into iPSC or partial iPSC and then expanded and differentiated into the desired cell types. The desired cell types include, without limitation, neurons, cardiomyocytes, blood cells, hepatocytes, pancreatic cells, muscle cells, lung cells, etc.

In one embodiment of the invention, the emerging colony selection decision is performed by the hierarchic decision method such as regulation tree (Lee, "Regulation of hierarchic decisions in intelligent systems", U.S. Pat. No. 7,031, 948, Apr. 18, 2006 and Lee, "Information integration method for decision regulation in hierarchic decision systems", U.S. Pat. No. 7,293,000, Nov. 6, 2007). Those ordinary skilled in the art should recognize that other pattern classification methods such as linear classifiers, support vector machines, quadratic classifiers, kernel estimation methods, boosting, artificial neural networks, gene expression programming, Bayesian networks, etc. are all within the scope of the current invention.

In another embodiment of the invention, the decision method does not output a crisp decision, that is binary ('Yes", "No") decision. Instead a score is output from the decision method. The score can then be thresholded for a binary decision. In this case, the threshold level can be used to control the sensitivity and specificity (or positive predictive value) of the decision output. In this embodiment, a threshold can be set to have very high positive predictive value even if the sensitivity is low. This allows the selection of just a few very high confident emerging colonies for continued processing.

D. Progressive Decision

The emerging colony 108 that is selected for continued processing by the emerging colony selection decision 222 will likely progress to the colony growing state 110. It can be further selected progressively by the growing colony state decision method described in the next section.

IV. Growing Colony State Decision

Figure 8:
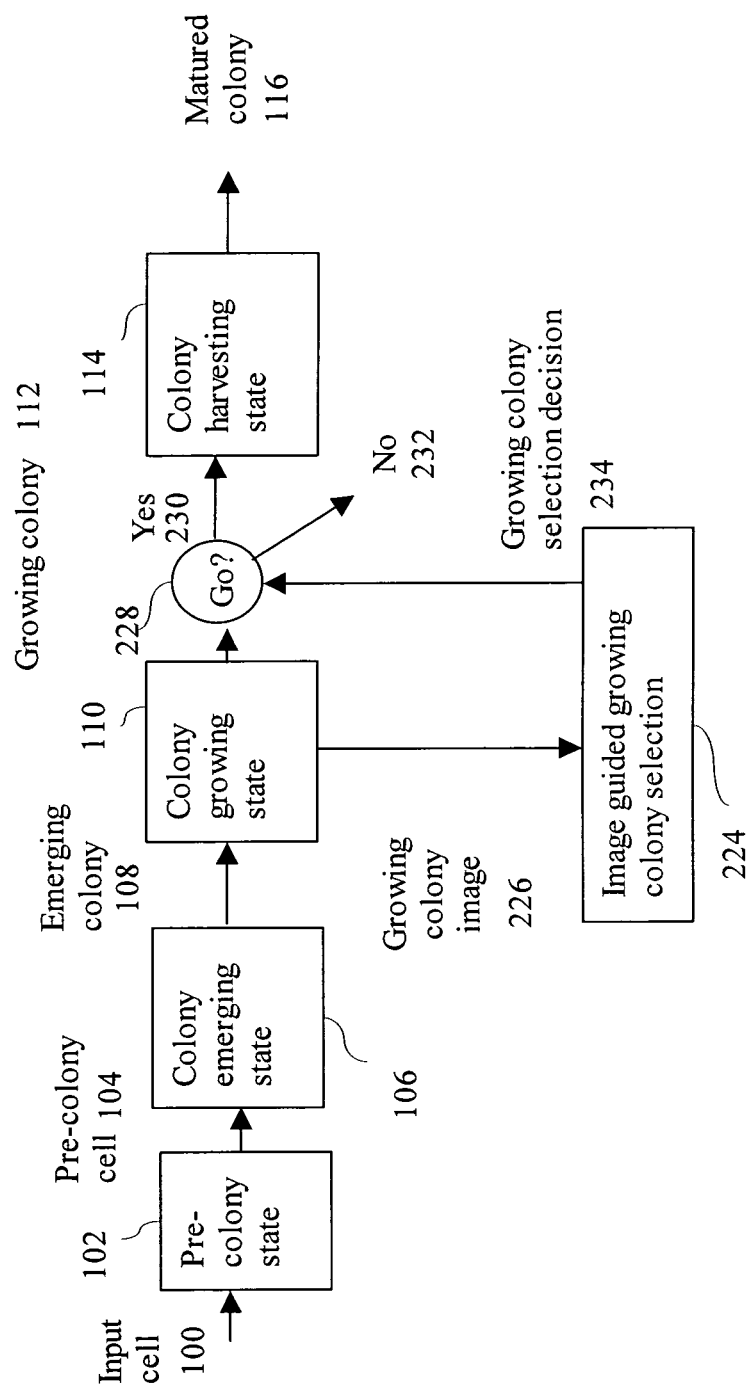
FIG. 8 shows the processing flow for the growing colony state decision method of the current invention.

The colony patterns in the colony growing state 110 can be used to perform growing colony selection decision 234 through an image guided growing colony selection 224 method. FIG. 8 shows the processing flow for the growing colony state decision of the current invention. The input cell 100 is reprogrammed to the colony growing state 110. A growing colony image 226 is acquired and processed by the image guided growing colony selection 224 step to generate a growing colony selection decision 234. The growing colony selection decision 234 is used to make a "Go" decision. 228 If the decision is "Yes" 230, the growing colony 112 is continued reprogrammed to reach the colony harvesting state 114. If the decision is "No" 232, no further selection decision will be made to the growing colony and depending on the assay protocol, the reprogramming may stop on the rejected growing colony to reduce wasteful processing cost.

IV.1 Overview

IV.2 Image Guided Growing Colony Selection

Figure 9:
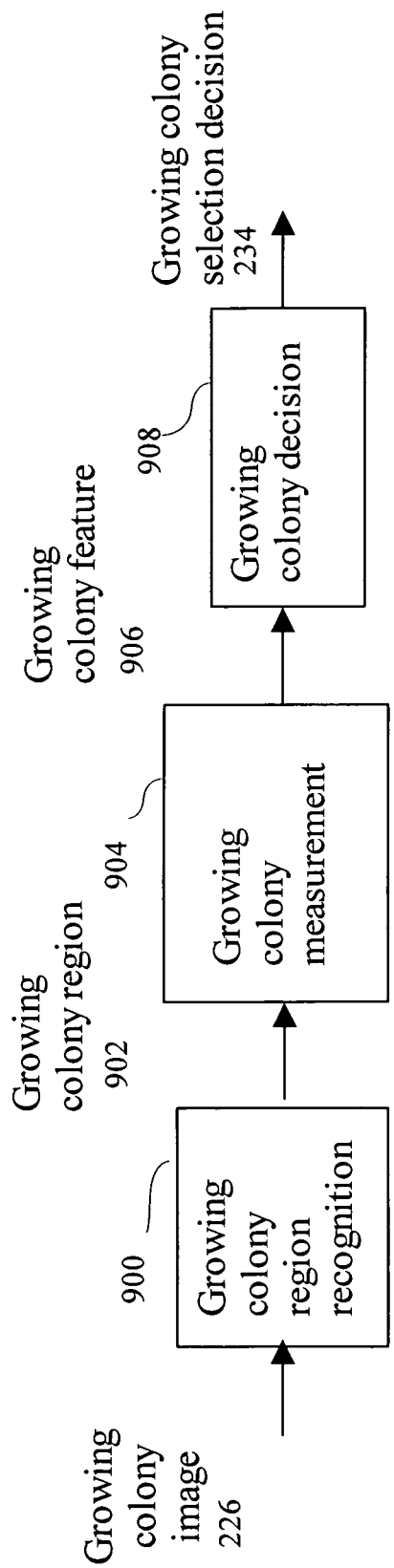
FIG. 9 shows the processing flow for the image guided growing colony selection method.

As shown in FIG. 9, a computerized image guided growing colony selection 224 method inputs at least one growing colony image 226. It performs growing colony region recognition 900 using the growing colony image 226 to generate growing colony region 902 output. It then performs growing colony measurement 904 using the growing colony region 902 to generate at least one growing colony feature output 906. At least one growing colony feature 906 is used to perform growing colony decision 908 that generates growing colony selection decision 234 output.

A. Growing Colony Region Recognition

Growing colony region recognition method performs growing colony detection to detect at least one growing colony. In one embodiment of the invention, the growing colony is detected using the learnable object segmentation method (Lee et al "learnable object segmentation", U.S. Pat. No. 7,203,360) and refined by the structure-guided image processing and image feature enhancement method (Lee, "Structure-guided image processing and image feature enhancement", U.S. Pat. No. 6,463,175) guided by the method of directed pattern enhancement (Lee et al, "Method of directed pattern enhancement for flexible recognition" U.S. Pat. Nos. 7,974,464 and 8,014,590).

To improve the growing colony detection accuracy, in another embodiment of the invention, the growing colony cell image further includes at least one additional image acquired in a later frame in colony growing state. Therefore, the growing colony detection of the early frame image can be guided by the growing colony in the later frame. An image alignment may be performed between the early and later frame images. After the alignment, the growing colony detection is performed within a region in early frame image that is in close proximity to the location of the corresponding colony in the later frame image. This also serves as a cross check of the growing colony detection in the later frame.

B. Growing Colony Measurement

Growing colony region is used to measure at least one growing colony feature from a set of growing colony features. In one embodiment of the invention, the growing colony region is divided into outside and inside regions. The outside region can be detected by a morphological erosion residue processing of the growing colony region or by image segmentation from outside in. The remaining region is the inside region. Features can be measured for outside and inside regions separately. The feature set includes morphological measures such as shape (compactness, elongateness, major-minor length ratio, Fourier descriptors, etc.) and size (area, perimeter, major and minor axis lengths, etc.); intensity measures (mean, median, standard variation, max, min, percentiles, etc.) and texture measures (co-occurrence matrix derived features, run-length derived features, wavelet derived features, fractal derived features, etc.). If there are more than one imaging modalities, such as phase contrast, DIC, fluorescence, luminescence and color channels. Color or multi-spectrum features can also be included for intensity and texture measures.

In addition, the ratio and difference for the features of outside and inside regions are calculated as the contrast features.

In the embodiment where the emerging colony cell image further includes at least one additional image acquired in a later frame in colony growing state 110, the temporal changes in growing colony features can be measured as the growth pattern temporal features. The measure of radius growth along the angular axis of the polar coordinate (mean and standard deviation) can reflect the rate of area change and the symmetry of the area changes. The symmetry of area changes is an especially important feature as some colonies form as the steady emergence of a small dense core. Other types of colonies emerge all at once, and from multiple regions.

If time-lapse image is available, the temporal measures include the starting time of the colony growing state 110 since the starting of the reprogramming and growing colony kinetic measures such as growth rate, growth structure, etc. The temporal measures could include temporal velocity (if at least 3 frames are available) and acceleration (if at least 4 frames are available) of the feature changes.

In addition, if 3D image is available the measures can be directly extended to 3D. For example all length measures are in 3D and area becomes volume.

If the growing colony 112 has previously passed the image guided emerging colony selection 212, the growing colony features can be enriched with the emerging colony features measured during the colony emerging state 106. The enriched feature set including both growing colony features and emerging colony features can be used in the growing colony selection decision 234.

C. Growing Colony Decision

The growing colony decision step uses at least one growing colony feature to make a growing colony selection decision 234. In one embodiment of the invention, the selection decision is reprogramming outcomes such as "iPSC" vs. "Non-iPSC". "iPSC" decision is for predicting growing colony 112 that is likely to be successfully re-programmed into induced pluripotent stem cells. "Non-iPSC" decision is for predicting growing colony 112 that is unlikely to be successfully re-programmed into induced pluripotent stem cells. In another embodiment of the invention, the selection decision is differentiation outcomes such as "Differentiable" vs. "Non-Differentiable". "Differentiable" decision is for predicting growing colony 112 that is likely to be successfully differentiated into the desired cell type(s). "Non-Differentiabe" decision is for predicting growing colony 112 that is unlikely to be successfully differentiated into the desired cell type(s). The differentiation can be performed either by direct programming that bypass the follow-on reprogramming process or by first reprogrammed into iPSC or partial iPSC and then expanded and differentiated into the desired cell types. The desired cell types include, without limitation, neurons, cardiomyocytes, blood cells, hepatocytes, pancreatic cells, muscle cells, lung cells, etc.

In one embodiment of the invention, the growing colony selection decision 234 is performed by the hierarchic decision method such as regulation tree (Lee, "Regulation of hierarchic decisions in intelligent systems", U.S. Pat. No. 7,031,948, Apr. 18, 2006 and Lee, "Information integration method for decision regulation in hierarchic decision systems", U.S. Pat. No. 7,293,000, Nov. 6, 2007). Those ordinary skilled in the art should recognize that other pattern classification methods such as linear classifiers, support vector machines, quadratic classifiers, kernel estimation methods, boosting, artificial neural networks, gene expression programming, Bayesian networks, etc. They are all within the scope of the current invention.

In another embodiment of the invention, the decision method does not output a crisp decision, that is a binary ('Yes", "No") decision. Instead a score is output from the decision method. The score can then be thresholded for a binary decision. In this case, the threshold level can be used to control the sensitivity and specificity (or positive predictive value) of the decision output. In this embodiment, a threshold can be set to have very high positive predictive value even if the sensitivity is low. This allows the selection of just a few very high confident growing colony for continued processing.

D. Progressive Decision

The growing colony 112 that is selected for continued processing by the growing colony selection decision 234 will likely progress to the colony harvesting state 114. It can be further selected progressively by the harvesting colony state decision method.

E. Harvesting Colony State Decision

The matured colony 116 in the colony harvesting state 114 can be further tested before picking and expansion to establish an iPSC line. In one embodiment of the invention, the harvesting colony state decision can be performed by image guided method similar to the growing colony state decision. In another embodiment of the invention, TRA-1-60 surface marker or viral GFP-silencing is imaged and used to detect iPSC colonies from non-iPSC ones. In yet another embodiment of the invention, the iPSC PCR Array is used to analyze multiple biologically validated pluripotency biomarkers to distinguish fully reprogrammed iPSC colonies from partially reprogrammed ones.

IV. Biological Cellular Process Progressive Selection

The progressive selection method of the current invention is applicable not only to iPSC reprogramming processes but also to biological cellular processes such as stem cell production, stem cell differentiation, cell culture production and cell transformation assays, etc.

Figure 10:
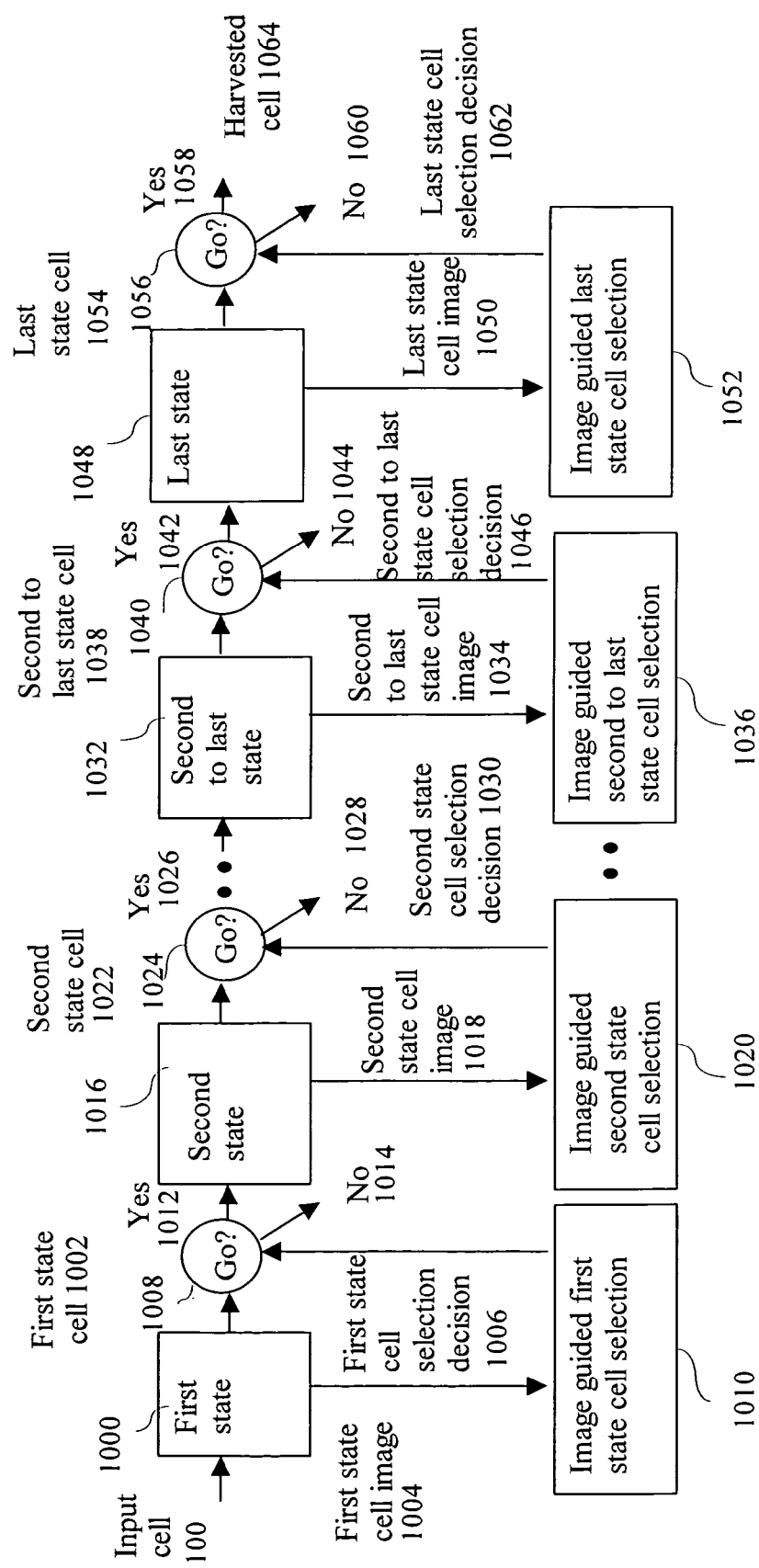
FIG. 10 shows the processing flow for the biological cellular process progressive selection method.

In a biological cellular process, a plurality of intermediate states can be defined. We call them first state, second state, etc. until second to last state and last state. The processing flow of the progressive selection method is shown in FIG. 10. During the first state 1000, first state cell image 1004 is subjected to image guided first state cell selection 1010. The first state cells 1002 with a decision outcome of "Yes" 1012 for the "Go" decision 1008 will continue the biological cellular and selection processes. The first state cells 1002 with decision outcome corresponding to "NO" 1014 in the "Go"

1008 decision will not be selected and the biological cellular process could continue or could be discontinued if it is practically convenient to do so. After the selected first state cells 1002 have progressed to the second state 1016, the second state cell image 1018 are subjected to image guided second state cell selection 1020. The second state cells 1022 (or colonies) with a decision outcome corresponding to "Yes" 1026 in the "Go" 1024 decision will continue the biological cellular and selection processes. The second state cells (or colonies) with decision outcome corresponding to "NO" 1028 in the "Go" 1024 decision will not be selected and the biological cellular process could continue or could be discontinued if it is practically convenient to do so.

The biological cellular and selection processes continue until the selected cells (or colonies) have progressed to the second to last state 1032. The second to last state cell image 1034 is subjected to image guided second to last state cell selection 1036. The second to last state cells 1038 (or colonies) with a decision outcome corresponding to "Yes" 1042 in the "Go" 1040 decision will continue the biological cellular and selection processes. The second to last state cells 1038 (or colonies) with decision outcome corresponding to "NO" 1044 in the "Go" 1040 decision will not be selected and the biological cellular process could continue or could be discontinued if it is practically convenient to do so. Similarly, after the selected second to last state cells 1038 (or colonies) have progressed to the last state 1048, the last state cells image 1050 is subjected to image guided last state cell selection 1052. The last state cells (or colonies) 1054 with a decision outcome corresponding to "Yes" 1058 in the "Go" 1056 decision will be harvested as the harvested cell 1064. The last state cells 1054 (or colonies) with decision outcome corresponding to "NO" 1060 in the "Go" 1056 decision will not be harvested.

Those ordinary skilled in the art should recognize that some of the intermediate selection steps could be skipped depending on the processes. In addition, the first selection step could start at any the processing states.

Figure 11:
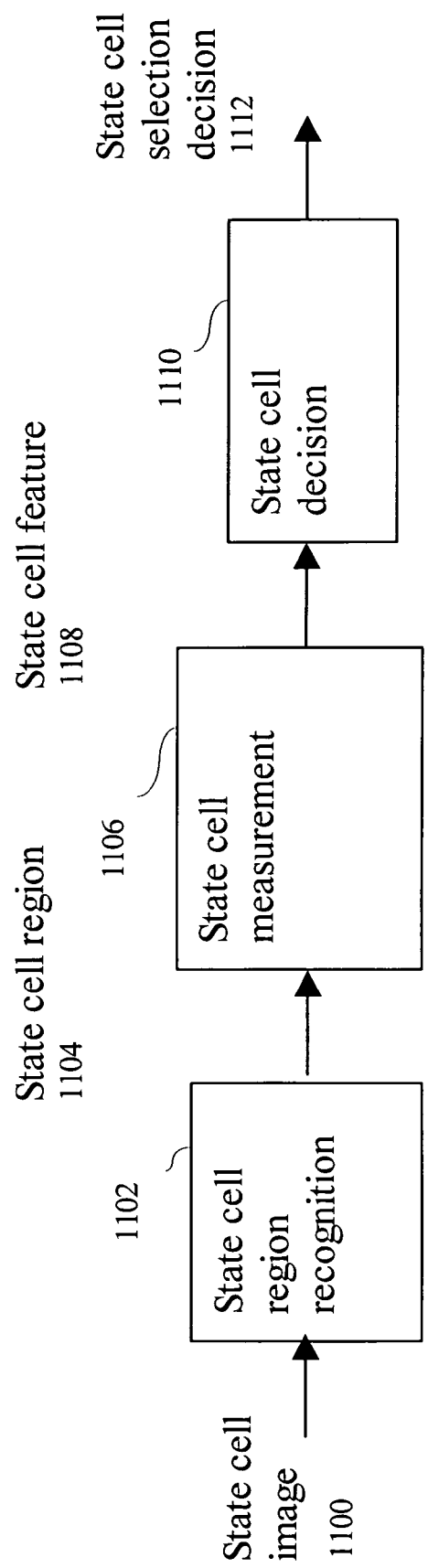
FIG. 11 shows the processing flow for the image guided state cell selection method at a given state.

As shown in FIG. 11, for a given state a computerized image guided state cell selection method inputs at least one state cell image 1100. It performs state colony region recognition 1102 using the state cell image 1100 to generate state cell region 1104 output. It then performs state cell measurement 1106 using the state cell region 1104 to generate at least one state cell feature 1108 output. At least one state cell feature 1108 is used to perform state cell decision 1110 that generates state cell selection decision 1112 output.

A. State Cell Region Recognition

State cell region recognition method performs state cell or colony detection to detect the region of the state cell or colony. In one embodiment of the invention, the state cell or colony is detected using the learnable object segmentation method (Lee et al "learnable object segmentation", U.S. Pat. No. 7,203,360) and refined by the structure-guided image processing and image feature enhancement method (Lee, "Structure-guided image processing and image feature enhancement", U.S. Pat. No. 6,463,175) guided by the method of directed pattern enhancement (Lee et al, "Method of directed pattern enhancement for flexible recognition" U.S. Pat. Nos. 7,974,464 and 8,014,590).

To improve the state cell or colony detection accuracy, in another embodiment of the invention, the state cell image further includes at least one additional image acquired in a later frame of the same state. Therefore, the state cell region detection of the early frame image can be guided by the state cell region in the later frame. An image alignment may be performed between the early and later frame images. After alignment, the state cell region detection is performed within a region in early frame image that is in close proximity to the location of the corresponding state cell region in the later frame image. This also serves as a cross check of the state cell region detection in the later frame.

B. State Cell Measurement

State cell or colony region is used to measure at least one State cell feature from a set of State cell features. In one embodiment of the invention, the feature set includes morphological measures such as shape (compactness, elongateness, major-minor length ratio, Fourier descriptors, etc.) and size (area, perimeter, major and minor axis lengths, etc.); intensity measures (mean, median, standard variation, max, min, percentiles, etc.) and texture measures (co-occurrence matrix derived features, run-length derived features, wavelet derived features, fractal derived features, etc.). If the state cell or colony region contains multiple components, the number of components and the multi-component structures can be measured. The multi-component structure measures include the population statistics (mean, median, standard deviation, etc.) of the size, shape, intensity and texture measures for the components as a group.

If there are more than one imaging modalities, such as phase contrast, DIC, fluorescence, luminescence and color channels. Color or multi-spectrum features can also be included for intensity and texture measures.

In the embodiment where state cell image further includes at least one additional image acquired in a later frame in the same state, the temporal changes in state cell features can be measured as the growth pattern temporal features.

If time-lapse image is available, the temporal measures include the starting time of the state since the starting of the process and state cell kinetic measures such as growth rate, growth structure, etc. The temporal measures could include temporal velocity (if at least 3 frames are available) and acceleration (if at least 4 frames are available) of the feature changes.

In addition, if 3D image is available the measures can be directly extended to 3D. For example all length measures are in 3D and area becomes volume.

The state cell features can be enriched with the previous state cell features measured during the previous states. The enriched feature set including both state cell features and previous state cell features can be used in the state cell decision.

C. State Cell Decision

The state cell decision 1110 step uses at least one state cell feature 1108 to make a state cell selection decision 1112. The selection decision could be reprogramming outcomes such as "iPSC" vs. "Non-iPSC" or differentiation outcomes such as "Differentiable" vs. "Non-Differentiable or cell production QA outcomes such as "Good quality" vs. "poor quality/reject" or cell transformation outcomes such as "success" or "failure", or "Continue" vs. "stop", etc.

In one embodiment of the invention, the state cell decision is performed by the hierarchic decision method such as regulation tree (Lee, "Regulation of hierarchic decisions in intelligent systems", U.S. Pat. No. 7,031,948, Apr. 18, 2006 and Lee, "Information integration method for decision regulation in hierarchic decision systems", U.S. Pat. No. 7,293,000, Nov. 6, 2007). Those ordinary skilled in the art should recognize that other pattern classification methods such as linear classifiers, support vector machines, quadratic classifiers, kernel estimation methods, boosting, artificial neural networks, gene expression programming, Bayesian networks, etc. are all within the scope of the current invention.

In another embodiment of the invention, the decision method does not output a crisp decision, that is binary ('Yes", "No") decision. Instead a score is output from the decision method. The score can then be thresholded for a binary decision. In this case, the threshold level can be used to control the sensitivity and specificity (or positive predictive value) of the decision output. In this embodiment, a threshold can be set to have very high positive predictive value even if the sensitivity is low. This allows the selection of just a few very high confident cells or colonies for continued processing.

Those ordinary skilled in the art should recognize that some of the intermediate selection steps could be skipped depending on the biological cellular processes. In addition, the first selection step could start at any the process states.

The invention has been described herein in considerable detail in order to comply with the Patent Statutes and to provide those skilled in the art with the information needed to apply the novel principles and to construct and use such specialized components as are required. However, it is to be understood that the inventions can be carried out by specifically different equipment and devices, and that various modifications, both as to the equipment details and operating procedures, can be accomplished without departing from the scope of the invention itself.

What is claimed is:

1. A computerized image guided pre-colony selection method comprising the steps of:
    a) Input into computer memory at least one pre-colony cell image;
    b) Perform by a computer pre-colony region recognition using the pre-colony cell image to generate pre-colony region context output;
    c) Perform by a computer pre-colony region context measurement using the pre-colony region context to generate at least one pre-colony region context feature output wherein the pre-colony region context feature is from a set consisting of seed cell features, adjacent region context features and background context features;
    d) Perform by a computer pre-colony decision using the pre-colony region context feature to generate pre-colony selection decision output.

2. The computerized image guided pre-colony selection method of claim 1 further includes at least one additional future-frame image acquired after colony is emerged for backward detection of pre-colony region.

3. The computerized image guided pre-colony selection method of claim 1 wherein the pre-colony decision makes selection decision of reprogramming outcomes "iPSC" vs. "Non-iPSC".

4. The computerized image guided pre-colony selection method of claim 1 wherein the pre-colony decision makes selection decision of differentiation outcomes "Differentiable" vs. "Non-Differentiable".

5. The computerized image guided pre-colony selection method of claim 1 wherein the pre-colony decision outputs a score that is thresholded for binary decision.

6. The computerized image guided pre-colony selection method of claim 2 wherein the pre-colony region context feature includes temporal measures of changes in seed cell features, adjacent region context features and background context features.

7. The computerized image guided pre-colony selection method of claim 1 wherein the pre-colony decision selected pre-colony is progressively selected in colony emerging state by emerging colony state decision method.

8. A computerized image guided emerging colony selection method comprising the steps of:
    a) Input into computer memory at least one emerging colony cell image;
    b) Perform by a computer emerging colony region recognition using the emerging colony cell image to generate emerging colony region output;
    c) Perform by a computer emerging colony measurement using the emerging colony region to generate at least one emerging colony feature output;
    d) Perform by a computer emerging colony decision using the emerging colony feature to generate emerging colony selection decision output;
    e) Include at least one additional image acquired in a later frame in colony emerging state for backward detection of emerging colony region.

9. The computerized image guided emerging colony selection method of claim 8 wherein the emerging colony decision makes selection decision of reprogramming outcomes "iPSC" vs. "Non-iPSC".

10. The computerized image guided emerging colony selection method of claim 8 wherein the emerging colony decision makes selection decision of differentiation outcomes "Differentiable" vs. "Non-Differentiable".

11. The computerized image guided emerging colony selection method of claim 8 wherein the emerging colony decision outputs a score that is thresholded for binary decision.

12. The computerized image guided emerging colony selection method of claim 8 wherein the emerging colony feature includes temporal measures of growth patterns.

13. The computerized image guided emerging colony selection method of claim 8 wherein the emerging colony decision selected emerging colony is progressively selected in colony growing state by growing colony state decision method.

14. A computerized image guided growing colony selection method comprising the steps of:
    a) Input into computer memory at least one growing colony cell image;
    b) Perform by a computer growing colony region recognition using the growing colony cell image to generate growing colony region output;
    c) Perform by a computer growing colony measurement using the growing colony region to generate at least one growing colony feature output wherein the growing colony feature includes features from outside region and from inside region and ratio and difference between features from outside and inside regions;
    d) Perform growing colony decision using the growing colony feature to generate growing colony selection decision output.

15. The computerized image guided growing colony selection method of claim 14 further includes at least one additional image acquired in a later frame in colony growing state.

16. The computerized image guided growing colony selection method of claim 14 wherein the growing colony decision makes selection decision of reprogramming outcomes "iPSC" vs. "Non-iPSC".

17. The computerized image guided growing colony selection method of claim 14 wherein the growing colony decision makes selection decision of differentiation outcomes "Differentiable" vs. "Non-Differentiable".

18. The computerized image guided growing colony selection method of claim 14 wherein the emerging colony decision outputs a score that is thresholded for binary decision.

19. The computerized image guided growing colony selection method of claim 15 wherein the growing colony feature includes temporal features of growth patterns.

20. The computerized image guided growing colony selection method of claim 14 wherein the growing colony decision selected growing colony is progressively selected in colony harvesting ready state by harvesting colony state decision method.

21. A computerized image guided biological cellular process progressive selection method comprising the steps of:
   a) Input into computer memory at least one state cell image;
   b) Perform by a computer state cell region recognition using the state cell image to generate state cell region output;
   c) Perform by a computer state cell measurement using the state cell region to generate at least one state cell feature output;
   d) Perform by a computer state cell decision using the state cell feature to generate state cell selection decision output wherein the state cell selection decision outputs a score that is thresholded for binary decision.

* * * * *